United States Patent

Noetzel et al.

[11] 4,010,225
[45] Mar. 1, 1977

[54] BROMINE CONTAINING TELOMERIC PHOSPHONIC ACID ESTERS AS FLAME RETARDANT AGENTS

[75] Inventors: Siegfried Noetzel, Kelkheim, Taunus; Horst Jastrow, Niederhochstadt, Taunus; Edgar Fischer, Frankfurt am Main, all of Germany

[73] Assignee: Hoechst Aktiengesellschaft, Frankfurt am Main, Germany

[22] Filed: Sept. 3, 1975

[21] Appl. No.: 610,087

Related U.S. Application Data

[62] Division of Ser. No. 478,262, June 11, 1974, Pat. No. 3,950,458.

[30] Foreign Application Priority Data

June 13, 1973 Germany .......................... 2329924

[52] U.S. Cl. ..................... 260/880 R; 260/45.7 P; 526/338; 526/340; 526/342
[51] Int. Cl.² ..................... C08K 5/53; C08L 9/02; C08L 9/06
[58] Field of Search ................ 260/45.7 P, 880 R

[56] References Cited

UNITED STATES PATENTS

| | | | |
|---|---|---|---|
| 3,700,760 | 10/1972 | Benghiat | 260/950 |
| 3,745,197 | 7/1973 | Toy et al. | 260/940 |
| 3,787,528 | 1/1974 | Benghiat | 260/865 |
| 3,830,886 | 8/1974 | Davis et al. | 260/953 |
| 3,896,187 | 7/1975 | Weil | 260/928 |
| 3,925,303 | 12/1975 | Rio et al. | 260/45.7 |

*Primary Examiner*—Donald E. Czaja
*Assistant Examiner*—R. A. White
*Attorney, Agent, or Firm*—Curtis, Morris & Safford

[57] ABSTRACT

Bromine containing telomeric phosphonic acid esters of the formula

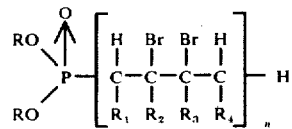

which are used as flameproofing agent for the preparation of flame-repellent thermoplastic compositions.

3 Claims, No Drawings

BROMINE CONTAINING TELOMERIC PHOSPHONIC ACID ESTERS AS FLAME RETARDANT AGENTS

This is a division, of application Ser. No. 478,262, filed June 11, 1974 now U.S. Pat. No. 3,950,458.

The present invention relates to bromine containing telomeric phosphonic acid esters.

It is known that easily flammable plastics may be flame-proofed by addition of halogen compounds. Flame-repellent plastics mixtures are important especially for the preparation of porous thermoplastic materials, for example cellular plastics made from styrene polymers.

Halogen compounds known as suitable flameproofing agents for plastics are for example high-degree chlorinated nonvolatile hydrocarbon compounds. They are preferably used together with antimony trioxide. However, the disadvantage resides in the fact relatively large amounts of the chlorinated hydrocarbons, generally from 15 to 20 weight % of the plastics amount, must be used to achieve a sufficient flame-repellent effect. This disadvantage is especially serious in the case of manufacture of foamed articles from expandable granular masses of thermoplastic materials, for the large amount of halogen compound makes bonding of the granular masses difficult. Very often, articles having a poor mechanical strength are obtained.

Furthermore it is known that organic bromine compounds are more efficient than the corresponding chlorine compounds, but all bromine compounds cannot be used as flame-repellent agents. Bromine compounds suitable for the flameproofing of plastics are for example tetrabromobutane, dibromo-ethylbenzene, dibromopropanol, tris(2,3-dibromopropyl)-phosphate, tetrabromocyclooctane or hexabromocyclododecane. They are generally used in amounts of from 5 to 10 weight % relative to the plastics amount.

A compound suitable as flameproofing agent for plastics has to possess above all the following properties: It has to be scarcely volatile and it must be odorless, it must not adversely affect the mechanical properties of the plastics, it must be most efficient in an amount as small as possible, and it must not provoke corrosion. It should be capable of being added to the monomer compounds already before the polymerization without adversely affecting the course of the subsequent polymerization. This requires the bromine compound to be well soluble in the monomer to be polymerized, for example styrene.

Organic bromine compounds the flame-repellent activity of which is known nearly never possess all these properties to a sufficient extent. Part of them are volatile, so that the flame-repellent properties of the plastics treated with them are lost after some time, part of them have an offensive smell, and many known bromine compounds have a plasticizing effect. For the manufacture of foamed articles from expandable granular masses of thermoplastic materials, however, flameproofing agents having plasticizing properties are inappropriate since they cause the obtention of foamed articles having insufficient pressure and volume strength. Moreover, most of the organic bromine compounds disturb the polymerization of monomeric polymerizable compounds. Therefore, they cannot be mixed with the monomers, but only with the finished plastics, and in many cases the solubility of the flameproofing agent in the polymerizable monomer, for example styrene, is very poor, so that it cannot be added during the polymerization. Other flameproofing agents, though being soluble in the polymerizable monomer, crystallize and separate because of incompatibility with the polymer, which results in a decreased non-flammability.

The present invention now provides novel bromine containing telomeric phosphonic acid esters of the formula

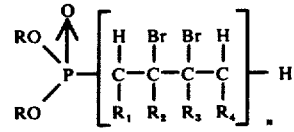

where R is a lower straight-chain or branched aliphatic hydrocarbon radical having from 1 to 8 carbon atoms; $R_1$ to $R_4$ are hydrogen, halogen, lower alkyl having from 1 to 4 carbon atoms, such as methyl, ethyl, n-propyl, isopropyl, n-butyl or isobutyl; and n is an integer of from 2 to 30.

It has furthermore been found that thermoplastic compositions possess excellent flame-repellent properties when they contain one of the above bromine telomeric phosphonic acid esters as flameproofing agent in such an amount that the bromine content of the mixture, relative to the plastic material, is from 0.3 to 20 weight %, preferably from 0.8 to 10 weight %.

The advantage of the telomeric phosphonic acid esters in accordance with the present invention resides in their good compatibility with polymers such as polystyrene. As compared to brominated butadiene polymers, the telomeric phosphonic acid esters have the advantage of being added in small amounts to the plastic material in order to obtain the same degree of non-flammability. As compared to brominated phosphonic acid esters, the telomeric phosphonic acid esters have a far superior stability to hydrolysis.

The bromine containing telomeric phosphonic acid esters are obtained from unsaturated telomeric phosphonic acid esters by bromination. The bromination may be carried out according to known methods. The brominated compounds are solid white substances and obtained for example by the action of a solution of bromine in chloroform on the unsaturated telomeric phosphonic acid estes dissolved in chloroform, at temperatures of from 0° to 10° C. The brominated products are isolated by precipitation in methanol. The unsaturated telomeric phosphonic acid esters are prepared by radical-forming telomerization of 1,3-dienes with dialkyl phosphites at temperatures of from 70° to 150° C, optionally with addition of chain transferring agents and under elevated pressure. Thus, for example, a telomeric phosphonic acid ester having a telomerization degree of about 20 and a phosphorus content of about 2.8% is obtained with good yield from 1 mole of butadiene-1,3 and 2 moles of diethyl phosphite in the presence of 6 weight % of di-tert.-butyl peroxide after heating to 150° C for 5 hours and after separation of the non-reacted diethyl phosphite.

The flame-repellent phosphonic acid esters according to this invention are odorless. They have practically no vapor pressure, do not volatilize therefore, and they are well compatible with a great number of plastics, for example polystyrene. Flame-repellent mixtures containing these flameproofing compounds do not lose their flame-repellent properties even after prolonged storage periods.

Using the compounds in accordance with the present invention, all easily flammable plastics, for example polymers and copolymers of ethylene, propylene, acrylonitrile, acrylic acid ester, methacrylic acid ester or vinyl acetate, or also curing resins, for example unsaturated polyester resins, or polyaddition compounds, for example polyurethanes, may be flameproofed. The compounds of the invention are especially appropriate for flameproofing styrene polymers such as polystyrene, or copolymers of styrene and acrylonitrile, or of styrene, butadiene-1,3 and acrylonitrile.

The flame-repellent mixtures may be prepared according to different methods. For example, homogeneous mixtures of the plastic material and the flameproofing agent of this invention may be prepared by mixing the plastic material and the bromine containing telomeric phosphonic acid ester at elevated temperatures, but below 170° C, in extruders or kneaders. It is also possible to dissolve both components in one common solvent and eliminate this solvent later on. An advantageous method is also the polymerization of monomer compounds in the presence of the flameproofing compounds. This method is especially important for the preparation of small particle flame-retarding and expandable styrene polymers by polymerization of styrene and easily volatile aliphatic hydrocarbons, and it is advantageously carried out in aqueous suspension. Other methods do not require a preliminary homogeneous mixture; in the case of granular or bead-shaped plastic compositions, the surface of the granules is coated, which operation mode is important in the case of expandable granular compositions, especially small particle expandable styrene polymers containing volatile aliphatic hydrocarbons as blowing agents. Some methods for preparing flame-retarding mixtures are also indicated in the following examples.

The following examples illustrate the invention; parts and percentages being by weight.

EXAMPLE 1:

30 parts of bromine containing telomeric phosphonic acid ester having a telomerization degree of 20, prepared from diethyl phosphite and butadiene-1,3 with subsequent bromination, and 4 parts of dibenzoyl peroxide are dissolved in 1000 parts of styrene. This solution is suspended in 2000 parts of water containing 8 parts of barium sulfate in a finely distributed form, and maintained at 70° C for 20 hours and at 80° C for 10 hours with agitation. Beads having a diameter of from 0.2 to 1.0 mm are formed in this operation step which are separated from the liquid. The product is molded at 160° C to form plates from which test samples having a dimension of 127 × 12.7 × 1.3 mm are cut. The test samples horizontally clamped are subjected at their loose ends for 30 seconds to a Bunsen flame burning with excess of oxygen. The flame extinguishes itself before reaching the first mark (at a distance of 25 mm from the loose end of the rod). According to the combustion test of ASTM D 635–68, the product is defined as being non-flammable.

EXAMPLE 2:

30 parts of bromine containing telomeric phosphonic acid ester having a telomerization degree of 20, prepared from diethyl phosphite and butadiene-1,3 with subsequent bromination, and 4 parts of dibenzoyl peroxide are dissolved in a mixture of 700 parts of styrene and 300 parts of acrylonitrile. The solution is suspended in 2000 parts of water containing 8 parts of barium sulfate as suspension stabilizer, and polymerized for 20 hours at 70° C and for 10 hours at 80° C. The polymer particles obtained are separated, washed and dried and molded at 160° C to form plates having a thickness of 1.3 mm, from which test rods having a dimension of 127 × 12.7 × 1.3 mm are cut. The test rods clamped horizontally are subjected at their loose ends for 30 seconds to a Bunsen flame burning with excess of oxygen. The flame extinguishes itself before reaching the first mark (at a distance of 25 mm from the loose end of the rod). According to the combustion test of ASTM D 635–68, the product is defined as being non-flammable.

EXAMPLE 3:

7000 parts of styrene in 24000 parts of water containing 120 parts of polyvinyl-pyrrolidone as protecting colloid and 5 parts of sodium pyrophosphate as buffer are polymerized with agitation with 550 parts of pentane and 30 parts of azo-diisobutyric acid nitrile in a 50 l pressure vessel for 40 hours at a temperature of from 60° to 90° C and under a nitrogen pressure of 3 atmospheres, until a bead-shaped mass is obtained. The reaction mixture is cooled and agitation is continued for a further 15 minutes after 30 parts of n-butanol are added. Subsequently, a mixture of 3000 parts of styrene and 700 parts of bromine containing telomeric phosphonic acid ester having a telomerization degree of 20, prepared from diethyl phosphite and butadiene-1,3 with subsequent bromination, 6 parts of azodiisobutyric acid nitrile and 150 parts of pentane, a mixture suspended in 3000 parts of water containing 40 parts of polyvinyl-pyrrolidone, is added to the reaction mixture, and, after a nitrogen pressure of 3 atm/g has been established, the whole is heated with agitation to 80°–90° C. A bead-shaped expandable styrol polymer is obtained which is foamed by means of steam. The foamed sample is subjected for 30 seconds to a Bunsen flame burning with excess of oxygen, and it extinguishes itself immediately after the flame is taken off.

EXAMPLE 4:

In a glass flask having a capacity of 1 liter, 230 ml each of demineralized vapor and styrene are introduced, heated to 90° C and the reaction is initiated by adding 0.7% of dibenzoyl peroxide, 0.12% of tert.-butyl-perbenzoate, 2.3 g of a bromine containing, telomeric phosphonic acid ester (0.65% of bromine), prepared from diethyl phosphite and butadiene-1,3 with subsequent bromination, 0.5 g of di-tert.-butyl peroxide, all dissolved in 45 ml of styrene.

After a conversion rate of 34% of polystyrene is obtained, a solution of 1 g of polyvinyl alcohol in 100 ml of water is added, which causes the formation of a stable dispersion. The polymerization is carried out for 10 hours at 90° C and for 3 hours at 115° C. After removal of the aqueous phase, the beadshaped polymer is washed with water and isolated. A sheet manufactured from this polymer is subjected for 30 seconds to a Bunsen flame burning with excess of oxygen. The sheet extinguishes itself immediately after the flame is taken off. The extinguishing time is less than 1 second.

EXAMPLE 5:

A 20% polystyrene solution in methylene chloride is prepared using polystyrene having a reduced specific viscosity of 1.4, 100 g of this solution are mixed with agitation with 0.2 g of a brominated telomeric phosphonic acid ester, prepared from diethyl phosphite and butadiene-1,3 with subsequent bromination, and 0.05 g of di-tert.-butyl peroxide, the mixture is poured into an aluminum foil formed as a cup and having a dimension of 19 × 6 × 2 cm. and stored for 12 hours under the fume hood. Subsequently, the aluminum foil is smoothened and placed in a polypropylene mold. After the polystyrene plate has been covered with a further aluminum foil, the whole is placed in a perforated steel mold and immersed for 20 minutes in boiling water. The foamed sheet is dried in a nitrogen atmosphere for 12 hours at 70° C and under a pressure of 400 mm.

The sheet is subjected for 30 seconds to a Bunsen flame burning with excess of oxygen, and, after the flame has been taken off, the sheet extinguishes itself within less than 1 second.

What is claimed is:

1. A flame-repellent thermoplastic composition comprising a thermoplastic polymer containing a flame repelling amount of a bromine-containing phosphonic acid ester of the formula

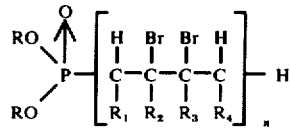

where R is a lower straight-chain or branched aliphatic hydrocarbon radical having from 1 to 8 carbon atoms; $R_1$ to $R_4$ are hydrogen, halogen or lower alkyl having from 1 to 4 carbon atoms; and n is an integer of from 2 to 30.

2. A composition according to claim 1 wherein the amount of bromine-containing phosphonic acid ester is such as to provide said composition with a bromine content of 0.3 to 20% by weight.

3. A composition according to claim 1 wherein said thermoplastic polymer is selected from polystyrene, copolymers of styrene and acrylonitrile, and copolymers of styrene, butadiene-1,3 and acrylonitrile.

* * * * *